US012112853B2

(12) United States Patent
Buvat

(10) Patent No.: US 12,112,853 B2
(45) Date of Patent: Oct. 8, 2024

(54) METHOD FOR ASSISTING WITH PROGNOSIS

(71) Applicants: INSERM (INSTITUT NATIONAL DE LA SANTÉ ET DE LA RECHERCHE MÉDICALE), Paris (FR); COMMISSARIAT A L'ENERGIE ATOMIQUE ET AUX ENERGIES ALTERNATIVES, Paris (FR); UNIVERSITE PARIS-SACLAY, Saint-Aubin (FR); CENTRE NATIONAL DE LA RECHERCHE SCIENTIFIQUE—CNRS—, Paris (FR)

(72) Inventor: Irène Buvat, Orsay (FR)

(73) Assignees: INSERM (INSTITUT NATIONAL DE LA SANTE ET DE LA RECHERCHE MEDICALE), Paris (FR); COMMISSARIAT A L'ENERGIE ATOMIQUE ET AUX ENERGIES ALTERNATIVES, Paris (FR); UNIVERSITY PARIS-SACLAY, Saint-Aubin (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 325 days.

(21) Appl. No.: 17/611,997

(22) PCT Filed: May 29, 2020

(86) PCT No.: PCT/EP2020/065055
§ 371 (c)(1),
(2) Date: Nov. 17, 2021

(87) PCT Pub. No.: WO2020/240009
PCT Pub. Date: Dec. 3, 2020

(65) Prior Publication Data
US 2023/0215572 A1    Jul. 6, 2023

(30) Foreign Application Priority Data

May 31, 2019 (EP) ..................... 19305697

(51) Int. Cl.
*G06N 3/08* (2023.01)
*G06T 7/00* (2017.01)
(Continued)

(52) U.S. Cl.
CPC ........... *G16H 50/30* (2018.01); *G06T 7/0014* (2013.01); *G16H 20/10* (2018.01); *G06T 2207/10104* (2013.01); *G06T 2207/30096* (2013.01)

(58) Field of Classification Search
CPC ........ A61B 6/502; G16H 50/20; G16H 10/40; G16H 50/30; G06T 7/0014; G06T 7/0012
See application file for complete search history.

(56) References Cited

U.S. PATENT DOCUMENTS

2018/0253591 A1    9/2018  Madabhushi
2020/0264416 A1*   8/2020  Hinnah .............. G02B 21/0036

FOREIGN PATENT DOCUMENTS

KR    2018 0128657 A    12/2018

OTHER PUBLICATIONS

Ceriani et al: "Metabolic heterogeneity on baseline 18FDG-PET/CT scan is a predictor of outcome in primary mediastinal B-cell lymphoma", Blood, vol. 132, No. 2, p. 179-186, Jul. 12, 2018.

(Continued)

*Primary Examiner* — Phuoc H Doan
(74) *Attorney, Agent, or Firm* — WC&F IP

(57) ABSTRACT

The present invention relates to a method for assisting with lymphoma prognosis. The prognosis of therapeutic response of patients with lymphoma is difficult. Based on a study of advanced stage DLBCL patients, the inventors showed that medical imaging such as 18F-FDG-PET/CT can provide a prognostic radiomic signature combining metrics reflecting tumor dissemination and tumor burden. In another aspect, the invention relates to a computer software comprising instructions to implement at least a part of a method according to the invention. In yet another aspect, the invention relates to a computer-readable non-transient recording medium on which a software is registered to implement a method according to the invention.

7 Claims, 1 Drawing Sheet

(51) Int. Cl.
*G16H 20/10* (2018.01)
*G16H 50/30* (2018.01)

(56) References Cited

OTHER PUBLICATIONS

Cottereau et al: "18FDG-PET dissemination features in diffuse large B cell lymphoma are prognostic of butcome", The Journal of Nuclear Medicine, Jun. 14, 2019.

Ilyas et al: "Defining the optimal method for measuring baseline metabolic tumour volume in diffuse large B cell lymphoma, European Journal of Nuclear Medicine", vol. 45, No. 7, pp. 1142-1154, Feb. 19, 2018.

Milgrom et al: "A Pet Radiomics Model to Predict Refractory Mediastinal Hodgkin Lymphoma", Scientifique Reports, vol. 9, No. 1, Feb. 4, 2019.

Parvez et al: "18-FDG PET/CT metabolic tumor parameters and radiomics features in aggressive non-Hodgkin's lymphoma as predictors of treatment outcome and survival", Annals of Nuclear Medicine, vol. 32, No. 6, p. 410-416, May 12, 2018.

Xie et al: "Predictive value of F-18 FDG PET/CT quantization parameters in diffuse large B cell lymphoma: a meta-analysis with 702 participants", Medical Oncology, Science and Technology Letters, vol. 32, No. 1, p. 1-10, Dec. 16, 2014.

* cited by examiner

METHOD FOR ASSISTING WITH PROGNOSIS

The present invention relates to the field of medical imaging, more specifically to the field of radiomic data analysis.

Diffuse large B-cell lymphoma (DLBCL) represents one of the most frequent types of lymphoid cancer, accounting for approximately 25% of non-Hodgkin lymphoma (NHL). The current first line treatment RCHOP—rituximab (R), a CD-20-directed monoclonal antibody, given in combination with CHOP, the standard chemotherapeutic regimen of cyclophosphamide, doxorubicin, vincristine and prednisone—is effective in 60% to 70% of patients. For the 30% to 40% of the patients who will exhibit refractory disease or relapse after initial response, the prognosis is poor. Their life expectancy is dramatically reduced since salvage regimens lead to very modest response rates. These patients still present a therapeutic challenge and a personalized approach might improve their prognosis. Interim PET (iPET) performed after 2 or 4 cycles of chemotherapy has been proposed as a tool for tailoring therapy but no therapeutic approach has proven successful to improve the prognosis of iPET positive patients. An earlier risk stratification is therefore still needed. High risk patients are not accurately identified by the current prognostic scoring system, based on the International Prognostic Index (IPI) and Ann Arbor classification. Over the last five years, the prognostic role of quantitative PET parameters, in particular the metabolic tumour volume (MTV), has been demonstrated in many lymphomas, including DLBCL. MTV reflects the total volume of 18F-FDG-avid tumour regions within the whole body, hence provides a more comprehensive tumour burden evaluation than previous surrogates such as lactate dehydrogenase levels. Patients with high tumour burden are at higher risk for treatment failure and shorter survival than those with low tumour burden. However, this parameter does not account for the spatial distribution of the lesions throughout the body.

Positon Emitting Tomography (PET) is a known technology which allows locating a radiotracer which has been previously injected in a patient.

Typically chosen radiotracers accumulate on the regions of the body which comprise cells with a high replication ratio.

Such regions include brain, liver and, most importantly, tumors.

PET scan imaging thus allows mapping the tumors of a patient which can be very useful in case of lymphoma for instance.

There already are databases which aggregate PET scan images of a high number of patients.

There is thus an interest in generating as much information it is possible to get out of these maps.

To this end, the present invention allows generating a prognosis indicator which can serve as a basis to estimate the chances of survival of the patient. Such indicator could also be used to determine the best suited treatment.

An object of the present invention is therefore a method for assisting with lymphoma prognosis comprising:
 providing imaging data of a patient presenting a lymphoma, preferably PET scan data,
 segmenting the imaging data so as to identify lesions,
 determining the distance between the two lesions which are furthest apart,
 determining the metabolic tumor volume, and
 providing a prognosis indicator based on the distance between the two lesions which are furthest apart.

Usable imaging data are preferably PET scan data. However, any imaging data can be used to this end.

As used herein, Lymphoma has its general meaning in the art and refers to a group of blood cancers that develop from lymphocytes. The term lymphoma includes all subtype lymphoma, i.e Hodgkin's lymphomas (HL) and non-Hodgkin lymphomas (NHL) such as diffuse large B-cell lymphoma (DLBCL).

Determining the distance between the two lesions which are furthest apart can be done either manually or using conventional image processing methods.

The metabolic tumor volume corresponds to the added volume of all the segmented lesions.

Although it is known that the more the lesions are spread over the body, the worse is the prognosis as far as lymphoma goes, no satisfying parameters had been found to actually characterize or measure the spreading of the lesions. Several parameters were tested such as the average distance between lesions had been considered but correlated badly with prognosis.

It has been found that, unexpectedly, the parameter which correlates best with the prognosis is actually quite simple to measure as it is the distance between the two lesions which are furthest apart. This parameter can be calculated simply and has significant correlation with the prognosis of the patients. The correlation has been found to be even higher when taking this parameter in combination with the metabolic tumor volume.

The invention therefore provides an easily doable method to obtain a prognosis for patients presenting a lymphoma. Such prognosis can be used to help the physicians adapt their treatment accordingly.

The segmentation is preferably based on a concentration of a tracing agent. Such tracing agent can be a radioisotope which concentration in the tissues correlates with their division rate. Since cancerous cells tend to have a higher division rate, the tracer concentration will be higher in cancerous regions.

However, there are cells which naturally have a high division rate and will consequently tend to accumulate a high concentration of tracer.

The segmentation can thus further comprise erasing regions with a naturally high concentration of tracing agent. Such regions include the brain or the hepatic region.

The method according to the present invention preferably further comprises a step consisting in providing help with the decisions between several medical treatments based on the prognosis indicator.

In that case, the several medical treatments can for instance comprise an RCHOP-type treatment and an RACVBP-type treatment. This can prove particularly helpful as RACVBP is more aggressive than the conventional RCHOP treatment and tend to induce heavier secondary effects for the patient. As such, physicians tend to avoid using RACVBP treatments in the absence of any additional data. Therefore, there is an interest in providing advises as per when such treatments are expected to yield better results than conventional RCHOP treatments.

Another object of the present invention is a computer software comprising instructions to implement at least a part of a method according to the invention when the software is executed by a processor.

Another object of the present invention is a computer-readable non-transient recording medium on which a software is registered to implement a method according to the invention when the software is executed by a processor.

The invention can be better understood at the reading of the detailed examples below, which constitute non-limitative embodiments of the present invention and at the examining of the annexed drawing, on which:

Figure 1:
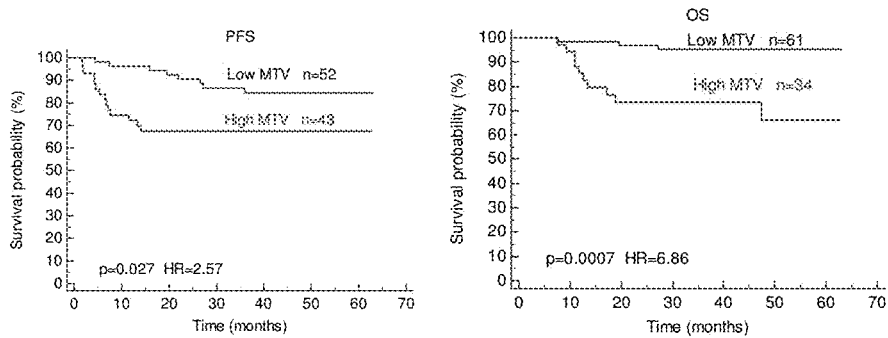
FIG. 1 is diagram showing the Kaplan-Meier estimates of progression-free survival (PFS) and overall survival (OS) according to metabolic tumor volume (MTV)
Figure 2:
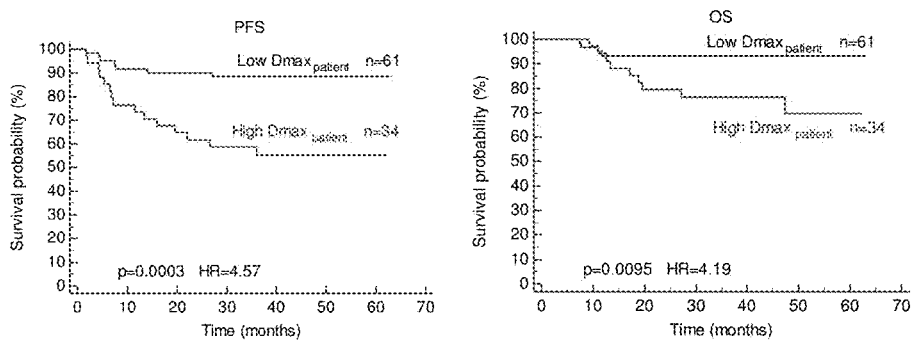
FIG. 2 is a diagram showing the Kaplan-Meier estimates of progression-free survival (PFS) and overall survival (OS) according to $Dmax_{patient}$.
Figure 3:
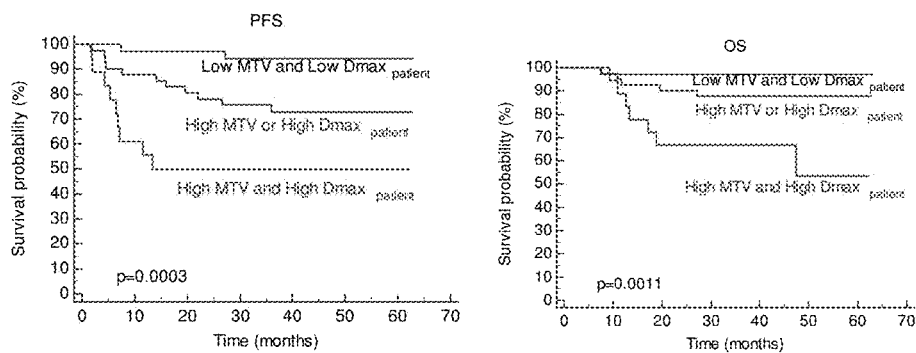
FIG. 3 is a diagram showing the Kaplan-Meier estimates of progression-free survival (PFS) and overall survival (OS) according to baseline metabolic tumour volume (MTV) and $Dmax_{patient}$.

It is understood that the described embodiments are not restrictive and that it is possible to make improvements to the invention without leaving the framework thereof.

Materials and Methods

Patients

DLBCL patients with an age adjusted IPI (aaIPI) score of 2 or 3 were randomly assigned to an induction immuno-chemotherapy with 4 cycles of either R-CHOP14 or R-ACVBP (rituximab, doxorubicin, cyclophosphamide, vindesine, bleomycin, prednisone). Consolidation treatment was driven by centrally reviewed PET assessment according to visual criteria after 2 and 4 treatment cycles. A baseline PET scan was mandatory, with at least one evaluable hypermetabolic lesion. Ethics approval was obtained for this trial, and all patients provided written informed consent to participate.

For the current analysis, only Ann Arbor stages 3 and 4 patients whose MTV could be computed from a baseline PET/CT scan and with at least two detectable lesions allowing distance measurement were included.

Baseline patient and disease characteristics, including individual components of the aaIPI score, progression-free survival (PFS) and overall survival (OS) defined according to the revised National Cancer Institute criteria were obtained.

PET/CT Scanning and Quantitative Analysis

Baseline PET image data in anonymized Digital Imaging and Communications in Medicine (DICOM) format was collected for functional parameter measurements. Quality control rejected scans with burning errors in DICOM retrieval or with a delay of >90 minutes between 18F-FDG injection and scanning.

Analysis of PET data was performed by a nuclear medicine physician blinded to patient outcome, using the software according to the invention. MTV was calculated based on a supervised segmentation of tumour regions involving 41% SUVmax thresholding of automatically detected hypermetabolic regions. MTV was defined as the sum of every individual lesion metabolic volume. For each lesion, the tumour lesion glycolysis was calculated as the product of the lesion volume by the SUV mean within the lesion, and the total lesion glycolysis (TLG) was obtained by summing the tumour lesion glycolysis over all lesions. The highest SUVmax of the patient over all lesions and the number of lesions were also reported. Last, several features reflecting the spatial distribution of malignant foci throughout the whole body were computed, based on distance measurements between lesions. Each lesion location was defined as the position of its center and the distances between two lesions were calculated using the Euclidian distance between their centers.

Four dissemination features were calculated: the distance between the two lesions that were the furthest apart (Dmaxpatient), the distance between the largest lesion and the lesion furthest away from that bulk (Dmaxbulk), the sum of the distances of the bulky lesion from all other lesions (SPREADbulk) and the largest value, over all lesions, of the sum of the distances from a lesion to all the others (SPREADpatient).

Statistical Analysis

For each PET-derived feature, Receiver Operating Characteristic (ROC) analysis was used to define the optimal cut-off for predicting the occurrence of an event (PFS or OS) by maximizing the Youden index (sensitivity+specificity−1). Sensitivity (Se) and specificity (Sp) were calculated for that cut-off value. Only features with an area under the ROC curve (AUC) greater than 0.6 on PFS were retained for subsequent analyses. Survival functions were calculated by using Kaplan-Meier analyses and the survival distributions were compared using the log-rank test. Multivariate analyses involving MTV and dissemination features were performed using Cox proportional hazard models. Based on these results, a prognostic model combining MTV and a dissemination feature was built on which Kaplan Meier survival analysis was performed. Correlations between dissemination features and MTV were assessed using chi-squared tests. Mann-Whitney tests were used to test whether the patient size and MTV were significantly different in patients with low and high dissemination features.

Statistical significance was set to $p<0.05$. All statistical analyses were performed using MedCalc software (MedCalc Software, Ostend, Belgium).

Results

In total, 95 patients, were included, whom clinical characteristics are summarised in Table 1.

TABLE 1

| Patient characteristics | |
| --- | --- |
| Patient characteristics | n = 95 (%) |
| Sex | |
| Female | 42 (44%) |
| Male | 53 (56%) |
| Age (median, ranges) years | 46 (18-59) |
| Height (median, ranges) cm | 173 (140-193) |
| ≤170 cm | 42 |
| >170 cm | 53 |
| Ann Arbor stage | |
| III | 9 (9.5%) |
| IV | 86 (90.5%) |
| Performance status | |
| 1 | 27 (28.4%) |
| 2 | 44 (46.3%) |
| 3 | 19 (20%) |
| 4 | 5 (5.3%) |
| aaIPI | |
| 1 | 3 (3%) |
| 2 | 69 (73%) |
| 3 | 23 (24%) |
| Treatment | |
| R-ACVBP 14 | 46 (48%) |
| R-CHOP 14 | 49 (52%) |

With a median follow-up of 44 months (range 27-63 months), the 4-year PFS and OS rates for the whole group were 77% and 85% respectively. Twenty-two patients had a PFS event with a median of 7 months, 12 in R-CHOP group and 10 in R-ACVBP group. Thirteen patients died with a median of 13 months, 8 in R-CHOP group and 5 in R-ACVBP group. Using log rank tests, neither performance status (0-1 versus 2-3) nor aaIPI (2 versus 3) were significantly associated with PFS (p=0.17, p=0.21) or OS (p=0.41, p=0.46). No significant prognostic impact of chemotherapy regimen (R-CHOP vs R-ACVBP) was observed for both PFS (p=0.69) and OS (p=0.48).

PET Features

Table 2 shows the descriptive statistics for the PET features and Table 3 gives the results of ROC analyses performed on each PET parameter.

(Table 3). Table4 shows that Dmaxpatient>58 cm, Dmaxbulk>43 cm, SPREADpatient>1020 cm and SPREADbulk>530 cm were negative prognostic factors for PFS (p=0.0003, p=0.0003, p=0.0011, p<0.0001 respectively) and that for OS, only Dmaxpatient and Dmaxbulk were statistically significant (p=0.0095 and p=0.023 respectively).

No significant differences in height were observed between patients with low and high Dmaxpatient (p=0.96). Similarly, no significant differences in MTV were observed between patients with low and high Dmaxpatient (median of 344 cm3 and 415 cm3 respectively, p=0.14).

TABLE 2

Median, range, mean and standard of deviation (SD) of PET features

| PET Parameters | PFS | | | | OS | | | |
|---|---|---|---|---|---|---|---|---|
| | AUC | Cut-off | Se | Sp | AUC | Cut-off | Se | Sp |
| MTV (cm$^3$) | 0.64 | 394 | 68 | 60 | 0.69 | 468 | 77 | 71 |
| SUVmax | 0.58 | 15 | 41 | 85 | 0.53 | 23 | 46 | 71 |
| TLG | 0.53 | 4396 | 45 | 68 | 0.67 | 4550 | 61 | 73 |
| Dmax$_{patient}$ (cm) | 0.65 | 58 | 68 | 74 | 0.59 | 58 | 69 | 69 |
| Dmax$_{Bulk}$ (cm) | 0.63 | 43 | 54 | 82 | 0.60 | 43 | 54 | 80 |
| SPREAD$_{patient}$ (cm) | 0.65 | 1023 | 50 | 85 | 0.58 | 716 | 54 | 71 |
| SPREAD$_{Bulk}$ (cm) | 0.65 | 530 | 54 | 86 | 0.59 | 407 | 61 | 71 |
| Nb of VOIs/patient | 0.64 | 23 | 54 | 77 | 0.57 | 20 | 54 | 67 |

| PET Parameters | median | range | mean | SD |
|---|---|---|---|---|
| MTV | 375 | 27-2525 | 469 | 392 |
| SUVmax | 20 | 4-49 | 21 | 8 |
| TLG | 3275 | 166-19428 | 4298 | 3323 |
| Dmax$_{patient}$ (cm) | 45 | 7-135 | 46 | 25 |
| Dmax$_{Bulk}$ (cm) | 32 | 7-101 | 32 | 17.5 |
| SPREAD$_{patient}$ (cm) | 367 | 7-11915 | 798 | 1420 |
| SPREAD$_{Bulk}$ (cm) | 205 | 7-4561 | 425.4 | 620 |
| Nb of VOIs/patient | 13 | 2-130 | 20 | 21 |

Table 3: ROC analysis of PET features, Area under the ROC curve (AUC), Sensitivity (Se), Specificity (Sp).

Using ROC optimal cut-off, MTV was highly predictive of outcome (PFS: p=0.027 and OS: p=0.0007) (Table 4). Patients with a high MTV had a significantly worse outcome with a 4-year PFS and OS of 67% and 73% versus 84% and 95% for patients with a lower MTV (FIG. 1).

Combination MTV and Dissemination Features

In multivariate Cox regression analysis including MTV and Dmaxpatient, Dmaxpatient was significantly associated with PFS (p=0.0014; HR=4.3) whereas MTV was borderline significant (p=0.056; HR=2.3). For OS, both factors remained significant (p=0.037 HR=4.0 for MTV and p=0.029; HR=3.7 for Dmaxpatient).

TABLE 4

PET parameters associated with PFS and OS in Log-rank Cox tests

| | PFS | | | OS | | |
|---|---|---|---|---|---|---|
| | HR (CI 95%) | 4y-PFS (CI 95%) | p | HR (CI 95%) | 4y-OS (CI 95%) | P |
| Low MTV | 1 (ref) | 84% (79-89) | 0.027 | 1 (ref) | 95% (92-98) | 0.0007 |
| High MTV | 2.6 (1.1-6.0) | 67% (60-74) | | 6.9 (2.1-21.9) | 66% (56-76) | |
| Low Dmax$_{patient}$ | 1 (ref) | 88% (84-92) | 0.0003 | 1 (ref) | 93% (90-96) | 0.0095 |
| High Dmax$_{patient}$ | 4.6 (1.9-11.2) | 55% (47-63) | | 4.2 (1.3-13.1) | 69% (60-78) | |
| Low Dmax$_{bulk}$ | 1 (ref) | 86% (82-90) | 0.0003 | 1 (ref) | 91% (88-94) | 0.023 |
| High Dmax$_{bulk}$ | 4.1 (1.5-11.3) | 52% (42-62) | | 3.3 (1-11.3) | 68% (57-79) | |
| Low SPREAD$_{patient}$ | 1 (ref) | 85% (81-89) | 0.0011 | 1 (ref) | 86% (81-91) | 0.24 |
| High SPREAD$_{patient}$ | 3.7 (1.3-10,1) | 52% (42-62) | | 1.9 (0.5-6.8) | 78% (70-85) | |
| Low SPREAD$_{bulk}$ | 1 | 86% (82-90) | <0.0001 | 1 (ref) | 90% (87-93) | 0.056 |
| High SPREAD$_{bulk}$ | 4.9 (1.7-13.9) | 45% (35-55) | | 2.8 (0.8-9.9) | 69% (59-79) | |
| Low nb of ROIs | 1 (ref) | 85% (81-89) | 0.0052 | 1 (ref) | 87% (82-92) | 0.21 |
| High nb of ROIs | 3.1 (1.2-7.9) | 58% (49-67) | | 1.9 (0.6-6.4) | 79% (72-86) | |

Regarding the dissemination features, ROC AUC were always greater than 0.6 for PFS, and close to 0.6 for OS Three risk categories could therefore be significantly distinguished on the basis of the presence or absence of high MTV (>394 cm3) or Dmaxpatient (>58 cm) (p=0.0003 for PFS and p=0.0011 for OS): group 1 with no risk factor (n=36), group 2 with one risk factor only (n=41), group 3 with both (n=18), with 4-year PFS rates of 94%, 73%, and 50%, respectively and 4-year OS rates of 97%, 88%, and 53%, respectively. Group 2 vs group 3 had significantly different PFS (p=0.041) and OS (p=0.019). Group 1 vs group 2 had significantly different PFS (p=0.013) whereas OS did not reach significance (p=0.13).

DISCUSSION

Lymphoma is a group of blood cancers that develop from lymphocytes. Although most cells in the body can migrate at one or more distinct steps during their development and differentiation, the trafficking propensity of lymphocytes is unrivaled among somatic cells. In case of malignant transformation, this property allows for rapid tumor dissemination irrespective of the conventional anatomic boundaries limiting early spread in most types of cancer. Thus, the disease can spread rapidly to different parts of the body, involving lymph nodes, possibly associated with extra nodal sites.

18F-FDG-PET/CT is the current state-of-the-art imaging scan in lymphoma. Recent advances in PET imaging revealed that MTV, as a surrogate for tumour cell number, has a strong prognostic value in DLBCL, much higher than the presence of a bulk. Recently, this was confirmed in a large phase 3 study, GOYA, including more than 1100 patients (NCT0128774): MTV quartiles stratified the population in quartiles 1, 2, 3 and 4 with a three-year PFS of 86%, 84%, 78% and 66% respectively. The present invention is based on the demonstration that MTV maintained its prognostic power in a cohort of advanced stage patients. Patients stage 3 or 4 were significantly stratified in two different risk categories according to their MTV. Moreover, using ROC analysis, MTV was the only significant feature on both PFS and OS. It was superior to standard features such as aaIPI for both PFS and OS. A high MTV identify 64% of the PFS events (14/22).

In this study, new radiomic features were introduced, extracted from PET scans to quantify tumour dissemination. Several of these features based on distance measurement between lymphoma lesions were significant for PFS and OS in a group of stage 3 and stage 4 patients, suggesting that an advanced characterization of the lesion dissemination is relevant even among patients with an advanced disease. In particular, the distance between the two lesions that were the furthest apart, Dmaxpatient, had strong predictive power for PFS and OS. A high Dmaxpatient was associated with an adverse outcome, with a 4-years PFS and OS of 55% and 69% respectively. Similarly, SPREADpatient and SPREADbulk combining spatial dispersion information and the number of lesion, were very significantly associated with PFS (Table 4).

Dmaxpatient is a very simple 3D feature to calculate with an intuitive interpretation. The height did not influence Dmaxpatient, as height did not significantly differ between high or low Dmaxpatient groups.

In multivariate analysis, MTV and Dmaxpatient remained independently significant for PFS and OS. The model combining these two factors was able to separate significantly three different prognostic groups: group 1 with no risk factor, group 2 with one risk factor, group 3 with both. Specifically, this could identify a group with a poor prognosis so that clinicians might consider changing treatment. Indeed, patients with high baseline MTV (>394 cm3) and high Dmaxpatient (>58 cm) had a much worse prognosis than the other patients with 4-year PFS 50% and 4-year OS 53%. This group represented 19% of the cohort and included 41% of the PFS total number of events (9/22) and 54% of the OS total number of events, making this model useful for identifying patients with poor prognosis.

In the LNH073B trial, consolidation treatment was driven by centrally reviewed PET assessment after 2 and 4 cycles: patients who were classified as PET 2 and PET 4 negative received standard immunochemotherapy consolidation; patients classified as PET 2 positive and PET4 negative received 2 cycles of high-dose methotrexate (3 g/m2) and then a high-dose therapy (carmustine, etoposide, cytarabine, melphal [BEAM] or zevalin, carmustine, etoposide, cytarabine, melphalan[Z-BEAM]), followed by Autologous Stem Cell Transplantation (ASCT); PET 4 positive patients had salvage regimen followed by ASCT in responders to salvage. Despite this 18F-FDG-PET-driven consolidation strategy that might actually decrease the prognostic impact of baseline PET features, MTV and dissemination features remained significantly predictive of PFS and OS. Further studies are needed to more comprehensively establish the role dissemination features might play in lymphomas when measured at baseline and during patient monitoring. Imaging of CXCR4 receptors could be helpful in this regard.

CONCLUSION

18F-FDG-PET/CT can provide a prognostic radiomic signature combining metrics reflecting tumor dissemination and tumor burden. In this study of advanced stage DLBCL patients, combining MTV and Dmaxpatient improved patient risk stratification at staging.

Unless otherwise specified, the word "or" is equivalent to "and/or". Similarly, the word 'one' is equivalent to 'at least one' unless the contrary is specified. Unless otherwise specified, all percentages are weight percentages.

The invention claimed is:

1. A computer implemented method for assisting with lymphoma prognosis comprising:
   providing imaging data of a patient presenting a lymphoma,
   segmenting the imaging data so as to identify lesions, wherein the segmentation further comprises erasing regions with a naturally high concentration of a tracing agent,
   determining a distance between the two lesions which are furthest apart,
   determining the metabolic tumor volume, and
   providing a prognosis indicator based on the distance between the two lesions which are furthest apart and on the metabolic tumor volume.

2. Method according to claim 1, wherein the provided imaging data are PET scan data.

3. Method according to claim 1, wherein the segmentation is based on a concentration of the tracing agent.

4. Method according to claim 1, further comprising a step comprising providing help with the decisions between several medical treatments based on the prognosis indicator.

5. Method according to claim 4, wherein the several medical treatments comprise an RCHOP-type treatment and an RACVBP-type treatment.

6. Computer software comprising instructions to implement at least a part of a method according to claim 1 when the software is executed by a processor.

7. Computer-readable non-transient recording medium on which a software is registered to implement a method according to claim 1 when the software is executed by a processor.

* * * * *